United States Patent [19]
Cao et al.

[11] Patent Number: 5,973,131
[45] Date of Patent: Oct. 26, 1999

[54] *PENICILLIUM MARNEFFEI* ANTIGENIC PROTEIN 1

[76] Inventors: Liang Cao, 76-1902 Bamboo Grove, 76 Kennedy Road; Kwok Yung Yuen, Flat D7, Block 26, Baguio Villa, 555 Victoria Road, both of Hong Kong, The Hong Kong Special Administrative Region of the People's Republic of China

[21] Appl. No.: 08/865,597

[22] Filed: May 29, 1997

Related U.S. Application Data

[63] Continuation-in-part of application No. 08/655,730, May 30, 1996, abandoned.

[51] Int. Cl.⁶ .......................... C07H 21/02; C07H 21/04; C12Q 1/68
[52] U.S. Cl. .............................. 536/23.1; 536/24.3; 435/6
[58] Field of Search ................................. 536/23.1, 24.3; 435/6; 530/350; 935/76, 77, 78

[56] References Cited

PUBLICATIONS

The Promega Catalog (1993/1994 Edition) p. 189.
Sommer et al., Nucleic Acids Research 17(16) : 6749 (1989).
The Promega Catalog (1993/1994 Edition) p. 92.
Chongtrakool et al., J. of Clinical Microbiology 35(9) : 2220–2223 (1997).
LoBuglio et al., J. of Clinical Microbiology 33(1) : 85–89 (1995).
Vanittanakom et al., J. of Clinical Microbiology 34(7) : 1834–1836 (1996).
Sundstrom and Aliaga (1992) Molecular Cloning c DNA and Analysis of Protein Secondary Structure of *Candida albicans* Enolase, an Abundant, Immunodominant Glycolytic Enzyme *Journal of Bacteriology* 174: 6789–6799. (Exhibit A).

Supparatpinyo et al. (1994) Disseminated *Pencillium marneffei* Infection in Southeast Asia. *The Lancet* 344: 110–113. (Exhibit B).

Yuen et al. (1994) Serodiagnosis of *Penicillium marneffei* Infection. *The Lancet* 344:444–446 (Exhibit C).

Walsh et al. (1991) Detection of Circulating Candida Enolase by Immunoassay in Patients with Cancer and Invasive Candidiasis. *The New England Journal of Medicine* 324: 1026–1031. (Exhibit D).

*Primary Examiner*—W. Gary Jones
*Assistant Examiner*—Ethan Whisenant
*Attorney, Agent, or Firm*—Robert D. Katz; Cooper & Dunham LLP

[57] ABSTRACT

Disclosed is a *Penicillium marneffei* PMAP1 polypeptide and DNA(RNA) encoding such PMAP1 polypeptide. Also provided is a procedure for producing such polypeptide by recombinant DNA techniques and a procedure for generating antibodies against the said polypeptide. Also disclosed is a method of using such polypeptide and the antibodies against it for the diagnosis of systemic infections of *Penicillium marneffei* by detecting the presence of the specific antibodies as well as the PMAP1 protein antigen in clinical specimens taken from suspected patients. Also provided are methods of using the PMAP1 DNA(RNA) or protein sequence to identify and to clone its homologous genes from other pathogenic fungi. Therefore, the identification of PMAP1 homologous genes from other pathogenic fungi are made possible with this invention. Also described is a therapeutic regimen using the antibodies against Penicillium infection. Also provided is a method of immunization against the infection of Penicillium.

9 Claims, 11 Drawing Sheets

A

```
  1  MKFLSSLVVL GLSAQALASP YVDHQATKDQ RDVNVFKQVL QDINLDVQKF

51  DQDITQYQGG DPTVLLADSD AIIKTTEEGI QRIGPQPPLS VTEALALVGP

101  VQGVNKLIMK AVDHLIEKKG PLVGGGYGPQ VKDSLERQAH AASKLSELVS

151  SKVPSPLAPI SKQLSDQVAQ ALQKGIQAFS ISARQATKVK REATKVQRDI

201  SAFKKVIQNI SLAVNKFNVD IERYVGGDAS HLLADGNVLI KATLDGVQSL
               *
251  QNEPPLSSME ALALVGPVQD LSNQILLAIQ NLIDKKEPLV QAGFGGKVEN

301  NLRQQEEAAQ KLSELVSTKV PHELADISRQ LSDGIAAGIK KGIDAFAGTG

351  PAPTTSSTPE ASTAPAPSTP PQTPEDTLVP ATSTPAPGPA PTAPDSSMVW

401  PTSTTASPDV QPTITSSGTS VPAAPTGGNS SPAVPAFTGA ASANQVSGAV
                                   *
451  GLAAGLLAVL AF
```

B

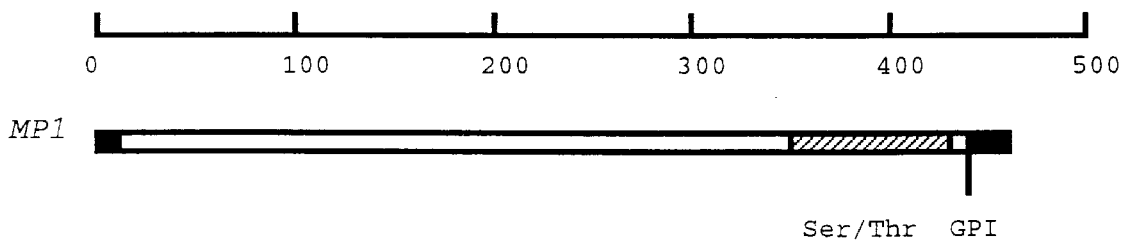

Figure 1. Mp1 protein sequence

PENICILLIUM MARNEFFEI ANTIGENIC PROTEIN 1

This application is a Continuation-In-Part application of U.S. Ser. No.08/655,730, filed May 30, 1996, and now abandoned the content of which is incorporated into this application by reference.

TECHNICAL FIELD OF INVENTION

This invention relates to a newly identified polynucleotide (gene), a polypeptide encoded by such polynucleotide, the use of such polynucleotide and polypeptide, as well as the production of such polypeptide. The polypeptide of the present invention is a novel protein that is produced by pathogenic fungus *Penicillium marneffei*. More particularly, the polypeptide of the present invention is *Penicillium marneffei* Antigenic Protein 1, sometimes hereinafter referred to as "PMAP1". The invention is related to the diagnostic, therapeutic, and prophylactic purpose of systemic infection by *Penicillium marneffei*. This invention is also related to the identification of polynucleotides, polypeptides of other pathogenic fungi that are homologous to the polynucleotide or polypeptide of the invention.

BACKGROUND ART

Systemic mycoses are very important infections in immunocompromised patients. In granulocytopenic patients following chemotherapy, bone marrow or organ transplant, Candida, Aspergillus and Mucoraceae cause serious fungal infections with current mortality rates of about 40% despite of the empirical anti-fungal therapy. In AIDS patients, Histoplasma for North America, Penicillium for Southeast Asia and Crytococcus occur most frequently. The mortality rate is usually very high.

The high mortality rate is partly due to the inability of making early, specific diagnosis of systemic fungal infections and therefore, the antifungal therapy is often delayed. Because of the low efficacy and high toxicity of antifungal drugs, there has been a significant limitation of prophylaxis with antifungal drugs (for review, J. L. Wheat, *Clinical Approach to Infection in the Compromised Host*, 3rd ed. Planum Medical Book Company, New York, 1994).

There has been a lack of specific test for the diagnosis of systemic fungal infections. Most of the fungal infections can not be easily diagnosed. With the exception of Cryptococcus that depends on the detection of fungal polysaccharide antigen in serum and Histoplasma in a crude cell extract (histoplasmin), the serology and antigen tests are virtually not effective in the diagnosis of systemic fungal infection due to the lack of sensitive and specificity.

Serology and antigen tests are most frequently used for the diagnosis of viral infections such as HIV and viral hepatitis. In all these cases, recombinant viral proteins and their antibodies are used for the tests. For most systemic fungal infections, however, the laboratory tests for diagnosis are usually unsatisfactory. Essentially all tests are made of crude antigens such as polysaccharides, therefore lack the desired specificity in most cases. Specific recombinant protein based diagnosis can be highly specific. Unlike viruses, however, pathogenic fungi are of far greater genomic complexity and most of the fungal genes can not be used for diagnosis. Therefore, to identify the very few good genes, if any, become the essence of this invention.

At present, the only fungal protein has been demonstrated to have very limited value in the diagnosis of the systemic fungal infection is Candida enolase (Walsh et al., New England Journal of Medicine, 324, 1026–1031). An enzyme assay was established for antigenaemia of enolase for the diagnosis of deep infection by Candida, however, there has been significant limitation in the sensitive of the assay. The application of such a test is very limited since tests on sequential specimens are needed to achieve only very moderate sensitive.

A year ago, it was reported in Lancet (Lancet 1994, 344, 444–5) about the serodiagnosis of *Penicillium marneffei* systemic infection. In that study, it was observed *Penicillium marneffei* infection in nearly 10% patients who have persistent fever despite multiple antimicrobials, and in 12% AIDS patients. Similar results were also obtained by Wong et al. at Queen Elizabeth Hospital in Hong Kong (Chung-Hua-I-Hsueh-Tsa-Chih-Taipei 1995, 55,127–36). The conventional method of diagnosis that depends on the isolation of the pathogen from blood specimens was very unsatisfactory, yielding only 10% success. Tissue biopsies were eventually obtained for the confirmation of diagnosis. The mean delay was 11 weeks. To solve the problem, it was established the serodiagnosis assay for *Penicillium marneffei* infection using immunofluorescent micrograph to determine the antibody titer against the fixed fungal cells. However, this assay requires special skills and equipment to perform. It is lengthy and technically more difficult. Most importantly, it is a very crude assay using whole cells as the antigen and therefore lacks adequate specificity.

*Penicillium marneffei* is one of the most important fungal pathogen in AIDS patients in Southeast Asia, including Thailand, Indonesia, Hong Kong and China. It was also reported in Europe and North America as imported pathogen carried by travelers. It causes disseminated infection which is always associated with non-specific symptoms including fever, anemia, weight loss and sometimes, skin lesions. In one of the more extensive recent studies done in Thailand (Lancet 1994, 344,110-3), 20% of AIDS people developed *Penicillium marneffei* infection. About half of the total cases (92) presented skin lesion which allowed the diagnosis through invasive procedures including bone-marrow aspirate and/or lymphoid and skin biopsies. The diagnosis was often delayed in patients who did not present skin lesions. Most patients who were diagnosed early responded to anti-fungal drugs, whereas most who were not diagnosed and treated died. Due to the high toxicity of anti-fungal drugs and the non-specific symptoms of *Penicillium marneffei* infection, early diagnosis is essential to achieve the cure.

SUMMARY OF THE INVENTION

The present invention solves the problem of diagnosing systemic infection of fungus *Penicillium marneffei* by identifying one of the most immunogenic protein produced by this fungus and by cloning the gene that encodes this protein. The recombinant protein of this gene as indicated in this invention has been shown to be of significant value in the diagnosis of *Penicillium marneffei* infection. The results in this invention indicates:

1. PMAP1 is a novel gene that shares absolutely no homology with any existing gene in the entire public gene data base.
2. The gene encodes a highly immunogenic protein for this fungus. The acute sera of immunocompetent patients with documented biopsy or culture positive Penicillium infection showed extremely high levels of specific antibodies against this protein, comparable to that of immunized animals. The levels of specific antibodies dropped very substantially one year after recovery.
3. HIV/*P. marneffei* patients showed lower levels of specific antibody than those *P. marneffei* patients who were free from HIV.

4. No cross reactivity with sera from other systemic mycoses patients was observed under high stringency wash condition, indicating the high specificity of the test.
5. PMAP1 protein was expressed as a GST-PMAP1 fusion protein. The fusion protein was purified from *E.coli* bacterial cells and specific antibodies were generated by immunizing animals.
6. An ELISA based Anti-PMAP1 Antibody Test using purified PMAP1 protein was produced and used for the detection of specific antibodies against PMAP1 protein in the *P. marneffei* infected patients' sera
7. The Anti-PMAP1 Antibody Test is effective for the detection of anti-PMAP1 antibodies in *P. marneffei* patients that were free from HIV. The test is sensitive and specific.
8. An ELISA based PMAP1 Antigen Test using two type of anti-PMAP1 antibodies to for a sandwich assay for PMAP1 protein.
9. The PMAP1 Antigen Test can be detected in the culture media of *P. marneffei* cells.
10. PMAP1 protein can be detected in serum samples of *P. marneffei* patients who are at late stages of AIDS.
11. Low stringency hybridization analysis indicated that PMAP1 is conserved among other pathogenic fungi, such as *Candida albicans* and *Candida tropicalis*.

In accordance with one aspect of the present invention, there are provided a novel mature polypeptide, as well as diagnostically or therapeutically useful fragments, analogs and derivatives thereof. The polypeptide of the present invention is of *Penicillium marneffei* origin.

In accordance with another aspect of the present invention, there are provided isolated nucleic acid molecules encoding the polypeptides of the present invention, including mRNAs, DNAs, cDNAs, genomic DNA as well as diagnostically or therapeutically useful fragments, analogs and derivatives thereof.

In accordance with still another aspect of the present invention, there are provided processes for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for diagnostic purposes, for example, the diagnosis of systemic infection by *Penicillium marneffei*. An immunoassay can be established using the recombinant protein for serological test of the presence of specific antibodies in the suspected patients' blood and urine, therefore, indicating the specific infection.

In accordance with yet another aspect of the present invention, there are provided methods of producing antibodies against such polypeptides. The antibodies can be polyclonal or monoclonal.

In accordance with yet another aspect of the present invention, the specific antibodies can be used for the detection of specific antigen (antigenaemia) of PMAP1 nature in specimens from suspected patients, including blood, urine, cerebra spinal fluid, and tissue biopsies. The presence of the protein antigen is indicative of current infection by *Penicillium marneffei*.

In accordance with yet another aspect of the present invention, the diagnostic test for antigenaemia may be used for the evaluation of the patients' response to anti-fungal treatments. A decrease in the antigen level in blood or urine can be an indicator of adequate response of patients during the treatment.

In accordance with yet another aspect of the present invention, the diagnostic test for antigenaemia may be used for the detection of potential relapse of the original pathogenic fungus after discontinuing anti-fungal treatment In accordance with yet another aspect of the present invention, the antibodies against PMAP1 protein may be used for the passive immunization or therapeutic purposes against the infection.

In accordance with yet another aspect of the present invention, there are provided a reagent for immunization which may be used to prevent the infection of *Penicillium marneffei* for the people at high risk.

In accordance with another aspect of the present invention, there are provided nucleic acid probes comprising nucleic acid molecules of sufficient length to specifically hybridize to nucleic acid sequences of the present invention. The probes can be used for the identification of homologous genes from Candida, Aspergillus, Mucoraceae, Cryptococcus, Histoplasma and Coccidioodes from either genomic DNA or cDNA libraries to identify the homologous genes.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 depicts the cDNA sequence and the corresponding deduced amino acid sequence of the polypeptide of the present invention (SEQ ID NO:1). The standard one letter abbreviations for amino acids are used. Sequencing accuracy is predicted to be greater than 98% (SEQ ID NO:2).

DETAILED DESCRIPTION OF THE INVENTION

The term "gene" means the segment of DNA involved in producing a polypeptide chain; it includes regions preceding and following the coding region (leader and trailer), as well as intervening sequences (introns) between individual coding segments (exons).

In accordance with one aspect of the present invention, there are provided isolated nucleic acid molecules (polynucleotides) which encode for the mature polypeptides having the deduced amino acid sequence of FIG. 1 for polypeptides which have fewer amino acid residues than those showing in FIG. 1.

A polynucleotide encoding a polypeptide of the present invention may be obtained from cDNA or genomic DNA libraries from *Penicillium marneffei*. The polynucleotide of this invention was discovered in a cDNA library derived from *Penicillium marneffei* through an antibody based, highly selective process as described in Example 1.

This polynucleotide encoding a polypeptide of the present invention can be obtained from cDNA or genomic DNA libraries from *Penicillium marneffei* using polynucleotide probes derived from SEQ NO:1 of this invention. Alternatively, it can be obtained by the amplification of either cDNA or genomic DNA from *Penicillium marneffei* through polymerase chain reaction (PCR) using appropriate polynucleotide primers derived from SEQ ID NO:1.

As described in Example 1, the PMAP1 gene encodes a highly abundant message RNA and produces a very immunogenic protein when the whole fungus was inoculated in Guinea pig. Amongst the ten cDNA phage clones isolated from 50,000 independent phage plaques of a *Penicillium marneffei* cDNA expression library using antibodies produced in Guinea pig, six of them encode full length PMAP1 gene. Sequence analysis indicated that they are independent isolates.

It is a novel gene. BLAST analysis (NCBI, National Library of Medicine) of both PMAP1 nucleotide and protein sequences against GCG data base failed to identify any significant homology with any existing gene. PMAP1 contains an open reading frame encoding a protein of 462 amino acid residues.

Figure 2:
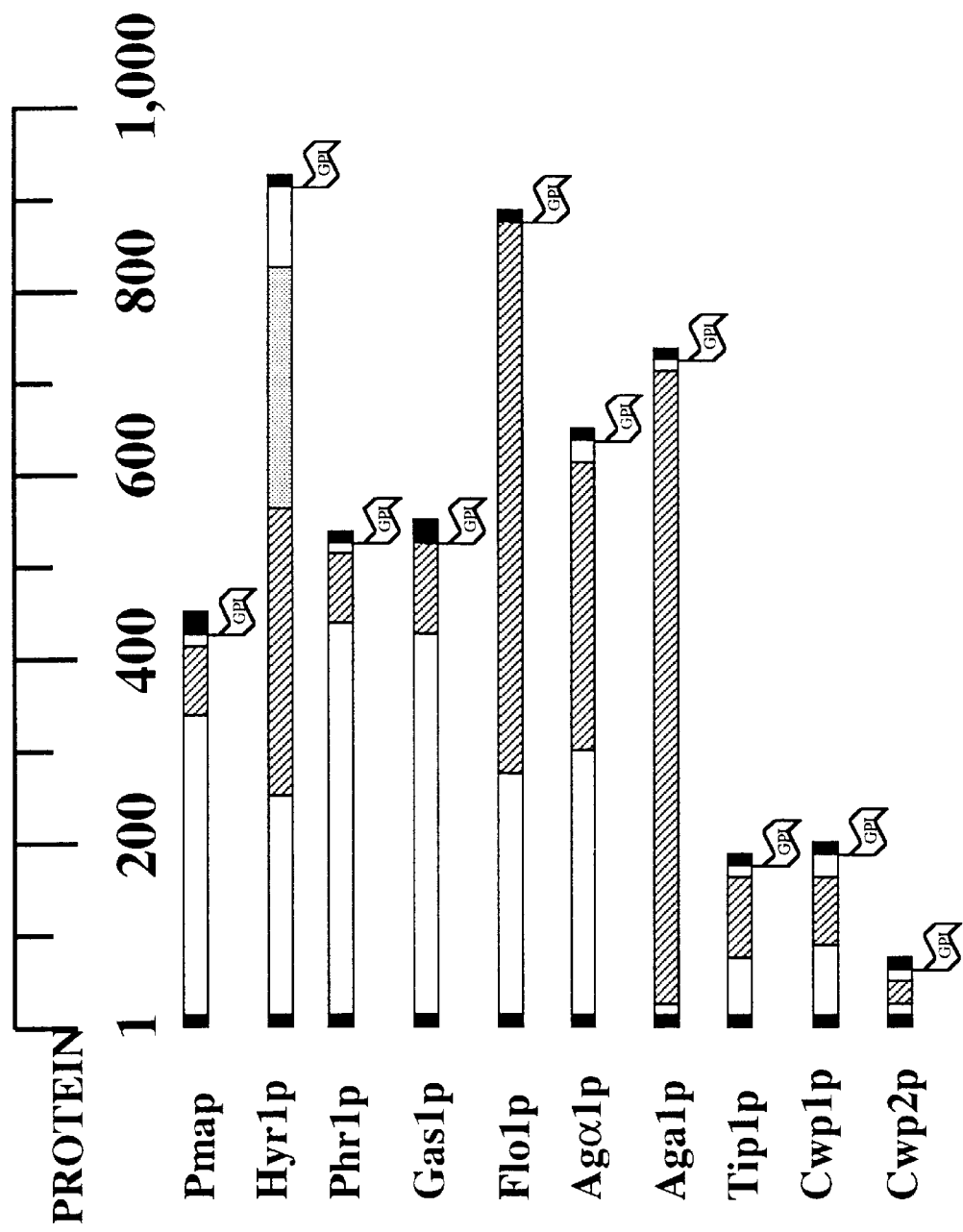
FIG. 2 depicts an illustration of the PMAP1 protein sequence motifs indicative of a cell wall protein of PMAP1 and its comparison with other cell wall proteins in yeast *Saccharomyces cerevisiae* and *Candida albicans*.

It is apparent that the protein contains several structure motifs that are common for yeast cell wall proteins, including a signal peptide at the N-terminus, and a GPI membrane anchoring motif at the C-terminus, suggesting that PMAP1 is localized on yeast cell wall (FIG. 2). In addition, PMAP1 contains a serine and threonine rich region at the C-terminal half, suggesting that the proteins is glycosylated. This is in consistent with the earlier observation that the patients' sera contain high titer of antibodies against cell surface components (K. Y. Yuen et al., The Lancet 344:444–5 (1994)).

Once processed, the matured PMAP1 polypeptide of the present invention is of 411 amino acid residues as shown in FIG. 2.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same mature polypeptide as the DNA of FIG. 1 or the deposited cDNA.

The term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-30 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

Fragments of the full length gene of the present invention may be used as a hybridization probe for a cDNA library to isolate the full length cDNA and to isolate other cDNAs which have a high sequence similarity to the gene. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen libraries of pathogenic fungi's cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringency conditions to the hereinabove-described polynucleotides. As herein used, the term "stringent conditions" means hybridization will occur only if there is at least 95% and preferably at 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of FIG. 1, for example, for recovery of the polynucleotide or as a diagnostic probe or as a PCR primer.

The present invention further relates to a polypeptides which have the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means any part of the polypeptide proteins as shown in FIG. 1.

The polypeptides of the present invention may be recombinant polypeptides, natural polypeptides or synthetic polypeptides, preferably recombinant polypeptides.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substitute group, or (iii) one in which the mature polypeptide is fused with another compound, such as a compound to increase the half-life of the polypeptide (for example, polyethylene glycol), or (iv) one in which the additional amino acids are fused to the mature polypeptide or (v) one in which comprises fewer amino acid residues shown in FIG. 1. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of FIG. 1 (in particular the mature polypeptide) as well as polypeptides which have at least 70% similarity (preferably at least 70% identity) to the polypeptide of FIG. 1 and more preferably at least 90% similarity (more preferably at least 95% identity) to the polypeptide of FIG. 1 and still more preferably at least 95% similarity (still more preferably at least 90% identity) to the polypeptide of FIG. 1 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the PMAP1 genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s)

(promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as E. coli Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-30 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), -factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The PMAP1 protein is produced in vitro and used for the testing of the presence of specific antibodies in serological samples from animals before and after *Penicillium marneffei* inoculation. As shown in Example 3, the PMAP1 polypeptide of FIG. 1 is produced by in vitro translation to give rise a polypeptide of 50 kd. This specific polypeptide is recognized specifically by serum from the animals that were inoculated with Penicillium as demonstrated by a positive band of 50 kd protein on a SDS-PAGE gel after immunoprecipitation assay. The serum from those before fungal inoculation, however, did not precipitate the 46 kd PMAP1 protein.

More importantly, the PMAP1 protein produced by in vitro translation can be specifically recognized by sera obtained from patients that have documented systemic *Penicillium marneffei* infection as described in Example 4. Those patients can be either Human Immunodeficiency Virus (HIV) serology positive or negative. The levels of specific antibodies against PMAP1 protein antibody in HIV seronegative Penicillium patients are at very high levels comparable to that of the immunized Guinea pig. Those from HIV seropositive Penicillium infected patients are somewhat lower but yet significantly higher than that of normal control people free from the infection. Interestingly, the sera specimens taken from HIV seronegative people who were previously infected by *Penicillium marneffei* but have been free of disease for at least one year after the original anti-fungal treatment at Queen Mary Hospital, Hong Kong showed remarkably reduced levels of the specific antibodies yet significant higher than that of the normal control cases. Therefore, a quantitative test can be established to detect the level of specific anti-PMAP1 antibody. A correlation between the levels of PMAP1 specific antibodies and CD4 positive T cell counts can also be established and used as a guide line for the serodiagnosis of *Penicillium marneffei* systemic infection in HIV positive patients. Thus, PMAP1 have been demonstrated to have the utility for the diagnosis of Penicilliosis by detecting the presence of specific antibodies against the PMAP1 protein in patients' sera.

In addition to its high sensitivity, this test using PMAP1 protein is also very specific. It is shown in Example 5 that sera from neither normal control (not infected) people, nor from those with some common systemic fungal infections, i.e. *Candida albicans*, have any detectable levels of the specific antibody against PMAP1.

PMAP1 polypeptides can be produced and isolated as described in Examples 6 and 7. and used for serological tests. The serological test for the presence of the specific antibody against PMAP1 can be of many different forms described herein and others within the limit of skill in the art, including but not limited to immunofluorescence, enzyme-linked immune assay, radio-immunoassay, complement fixation test, latex agglutination test, precipitation, immunodiffusion test, neutralization test, skin test and other methods derived from them.

An example of ELISA assay (Coligan, et al., Current Protocols in Immunology, 1(2), Chapter 6, (1991)) initially comprises the purified recombinant protein coated on the solid phase polystyrene dish. In addition a reporter antibody is prepared against the human antibody. To the reporter antibody is attached a detectable reagent such as radioactivity, fluorescence or, in this example, a horseradish peroxidase enzyme. First, the polystyrene dish is coated with the recombinant protein. Next, a blood sample is removed from a suspected patient and incubated in the dish during which time the specific human antibodies against PMAP1 can bind to any PMAP1 proteins coated onto the polystyrene dish. All unbound human antibodies are washed away with buffer. A reporter antibody linked to horseradish peroxidase is placed in the dish resulting in binding of the reporter antibody to any human antibody bound to PMAP1. Unattached reporter antibody is then washed out. Peroxidase substrates are then added to the dish and the amount of color developed in a given time period is a measurement of the titer of PMAP1 antibody present in a given volume of patient sample. Examples 9 and 10 illustrate such work and the result of work in diagnosis of *P. marneffei* infections.

PMAP1 nucleic acid sequences and PMAP1 polypeptides may also be employed for in vitro purposes related to scientific research and diagnosis of the disease. For example, Polymerase Chain Reaction (PCR) can be used for the identification and diagnosis of the infection.

The polypeptides, their fragments or other derivatives, or analogs thereof, or cells expressing them can be used as an immunogen to produce antibodies thereto as described in example 8. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

It was important to explore the possibility of a test for PMAP1 protein for the diagnosis of *P. marneffei* infections. In order to examine the subcellular localization of PMAP1 protein, immunogold electron microscopic work was carried to confirm the potential cell wall localization as suggested by the protein sequence. Example 11 illustrated the cell wall localization of PMAP1 protein.

The specific antibodies can then be used for the detection of Penicillium antigen from the suspected patients' blood or urine. Assays used to detect levels of PMAP1 protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the PMAP1 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, such as, bovine serum albumen. Next, the monoclonal antibody is incubated in the dish during which time the monoclonal antibodies attach to any PMAP1 proteins attached to the polystyrene dish. All unbound monoclonal antibody is washed out with buffer. The reporter antibody linked to horseradish peroxidase is placed in the dish resulting in binding of the reporter antibody to any monoclonal antibody bound to PMAP1. Unattached reporter antibody is then washed out. Peroxidase substrates are then added to the dish and the amount of color developed in a given time period is a measurement of the amount of PMAP1 protein present in a given volume of patient sample when compared against a standard curve.

The ELISA test was set up using purified recombinant PMAP1 protein as indicated in Example 12. The evaluation of such a sandwich test was done first with purified recombinant GST-PMAP1 protein. Using the cell culture media of *P. marneffei*, it was further indicated that PMAP1 is present in large amount in the culture media of *P. marneffei* cells as shown in Example 13. Finally, in Example 14, it was demonstrated that circulating PMAP1 antigens can be specifically detected in the serum and urine samples of *P. marneffei* patients with AIDS. The test is specific since none was shown to be positive for 100 normal blood donors.

A competition assay may be employed wherein antibodies specific to PMAP1 are attached to a solid support. Polypeptides of the present invention are then labeled, for example, by radioactivity, and a sample derived from the host are passed over the solid support and the amount of label detected, for example by liquid scintillation chromatography, can be correlated to a quantity of PMAP1 in the sample.

A "sandwich" assay is similar to an ELISA assay. In a "sandwich" assay PMAP1 is passed over a solid support and binds to antibody attached to a solid support. A second antibody is then bound to the PMAP1. A third antibody which is labeled and specific to the second antibody is then passed over the solid support and binds to the second antibody and an amount can then be quantified.

The levels of PMAP1 antigen in patients' specimens can be used an indicator of treatment response during the clinical management of *Penicillium marneffei* infected patients. The levels of fungal PMAP1 antigen in patient blood and urine can be continuously monitored with the above proposed antigen test after the initiated anti-fungal drug treatment. A decrease in the antigen level can be a good indication of adequate response after treatment. Persistent high levels of the antigen can be used to suggest an alternative anti-fungal drug treatment. An initial decrease followed by a later increase of the PMAP1 antigen level can be indicative of relapse of the infection.

The antibody can also be used for the identification of the pathogenic fungus from tissue biopsies, blood, bone marrow, cerebra-spinal fluid and other specimens of the suspected patients. The presence of PMAP1 specific antigen in the clinical specimens are indicative of current infection of the suspected patients.

The antibody can also be used for therapeutic purpose. It was shown that in immunocompetent penicilliosis patients and in animal that were injected with *Penicillium marneffei*, very high levels of specific antibodies against PMAP1 were detected. These are real reflections of biological responses against the infection by this pathogenic fungus. The administration of high levels of antiserum against PMAP1 may be of significant value as a passive immunization, or therapeutic regimen against the infection by *Penicillium marneffei*.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the intravenous, intraperitoneal, intramuscular, subcutaneous, or intradermal routes. The pharmaceutical compositions are administered in an amount which is effective for treating and/or prophylaxis of the specific indication. In general, the pharmaceutical compositions are administered in an amount of at least about 10 mg/kg body weight and in most cases they will be administered in an amount not in excess of about 8 mg/Kg body weight per day. In most cases, the dosage is from about 10 mg/kg to about 1 mg/kg body weight daily, taking into account the routes of administration, symptoms, etc.

PMAP1 protein can be used for immunization purpose of the high risk people. Since *Penicillium marneffei* is acquired by inhalation of infectious canidia, immunization through mucosal route to stimulate the production of secretary IgA.

The specific IgA could have neutralizing activity on the infectious canidia by preventing the adherence of the fungus on to the surface of the host cells that represents the very first step of fungal invasion. Similarly, the immunization with PMAP1 protein can generate cell mediated immune response that include the activation of helper T cells and cytotoxic T cells. Because PMAP1 produces very high level of antibody response in both animals and infected patients, it is conceivable that the immune response against this specific protein can have protected function against infection.

The immunization can be carried out as recommended by the Immunization Practices Advisor Committee (MMWR 1990. 39:1 No. RR-2). Vaccines are given at doses between 10 ug to 1 mg per adult each time. Three injections spaced by one month and six months are suggested. Seroconversion will be tested after the end the final vaccination.

Fragments of the full length PMAP1 gene may be used as a hybridization probe in DNA library screening to isolate similar genes which have high sequence similarities to PMAP1 from many other pathogenic fungi that also cause systemic infection in human. An alternative approach is to generate specific antibodies against PMAP1 and use the antibodies to clone these genes. These pathogenic fungi include: Candida, Aspergillus, Mucoraceae, Cryptococcus, Histoplasma and Coccidioodes. The DNA libraries can be either cDNA or genomic libraries.

An example of the screening comprises the isolation of homologous gene by low stringency nucleotide hybridization using the whole or any part of the coding sequence of the PMAP1 gene shown in FIG. 1. Labeled PMAP1 probes having sequences identical or complementary to that of the gene of the present invention are used to screen libraries of other fungi cDNA or genomic DNA libraries to identify and isolate the clones that hybridize to the probe. The hybridization can be carried out at low stringency condition. An example of the condition of hybridization is to incubate the labeled probes with the libraries overnight at 42° C. in a hybridization solution containing 5×SSC, 35% formamide, 5×Denhardts'; solution, 250 ug/ml carrier DNA, 50 mM NaPO4 and 1% SDS. Washes are done with 1×SSC, 0.1% SDS for twice at room temperature and twice at 37° C.

Example 6 demonstrated the potential presence of such homologous genes in *Candida albicans* and Candida Tropicalis and a method of low stringency hybridization for the detection of such homologous genes in these organisms using the method described above. It is the work of the art to use the above procedure or procedures of similar nature to isolate genes from other pathogenic fungi that are homologous to PMAP1.

Any gene of other infectious fungi identified using the full or any part of the PMAP1 DNA, RNA, protein sequence or antibodies generated against the PMAP1 protein will be considered homologous gene. All the work leading to the identifying and cloning of its homologous genes are considered the work of the art only possible with the knowledge from this invention. Those homologous gene products (recombinant proteins) can then be produced and isolated using above suggested protocol. The recombinant protein can then be used for serological tests for the presence of specific antibodies and antigen test in the suspected patients described above. Other applications against all other fungal infections using PMAP1 gene homologous genes, included but not limited to all the claims of this invention are only possible with the knowledge of this invention.

More importantly, this invention also provided a method of using fungal-immunizing animal sera for the screening of cDNA expression libraries made from pathogenic fungi. The animals herein included specifically Guinea pig and mouse. Previously, people used human fungal infected patients' sera for the screening of fungal libraries with little success. The method of using immunized animal sera disclosed in Example 1 to screen a cDNA expression library has unique advantages of low background and high specificity. This invention demonstrated the similarities of the specific antibodies produced from both human and Guinea pig after whole pathogenic fungal cell inoculation, which became the basis of using animal sera for screening.

This invention further provides a method of identifying *Penicillium marneffei* Antigenic Protein 1 homologous genes from a fungus other than *Penicillium marneffei* comprising steps of: a) obtaining a DNA library containing clones having inserts specific for a fungus other than *Penicillium marneffei*; b) hybridizing the clones in the library with at least one specific probe for *Penicillium marneffei* Antigenic Protein 1 gene under conditions permitting hybridization of the specific probe to a *Penicillium marneffei* Antigenic Protein 1 homologous gene; and c) isolating clones capable of hybridizing to the probe; d) determining the DNA sequence of the inserts; e) comparing the homology in sequence between the *Penicillium marneffei* Antigenic Protein 1 gene and the inserts to confirm the identity of the homologous gene. In an embodiment of the above method, it further comprises after step (d), determining the protein sequence encoded by the inserts and comparing the sequence homology of the determined protein sequence with the sequence of *Penicillium marneffei* Antigenic Protein 1.

This invention also provides a method of identifying *Penicillium marneffei* Antigenic Protein 1 homologous genes from a fungus other than *Penicillium marneffei* comprising steps of: a) obtaining an expression cDNA library containing clones having inserts specific for a fungus other than *Penicillium marneffei*; b) contacting the clones with at least one antibody capable of specifically binding to PMAP1 or its homologous proteins under conditions permitting the binding of said antibody to *Penicillium marneffei* Antigenic Protein 1; c) isolating clones capable of binding to said antibody; d) determining the DNA sequence of the inserts; and e) comparing the homology in sequence between the *Penicillium marneffei* Antigenic Protein 1 gene and the inserts to confirm the identity of the homologous gene which codes for a homologous *Penicillium marneffei* Antigenic Protein 1. In an embodiment of the preceding method, it further comprises after step (d), determining the protein sequence encoded by the inserts and comparing the sequence homology of the determined protein sequence with the sequence of *Penicillium marneffei* Antigenic Protein 1.

This invention provides the isolated *Penicillium marneffei* Antigenic Protein 1 homologous gene identified by the above methods.

This invention also provides nucleic acid molecules of at least 15 nucleotides capable of specifically hybridizing with a unique sequence of the *Penicillium marneffei* Antigenic Protein 1 homologous genes.

This invention provides an isolated *Penicillium marneffei* Antigenic Protein 1 homologous protein. This invention also provides an antibody capable of specifically binding to the *Penicillium marneffei* Antigenic Protein 1 homologous protein.

This invention provides a method for measuring the amount of *Penicillium marneffei* Antigenic Protein 1 homologous protein in a sample comprising steps of: a) contacting the sample with the antibody capable of specifically binding to the *Penicillium marneffei* Antigenic Protein 1 homologous protein under conditions permitting formation of complexes between said antibody and *Penicillium marneffei* Antigenic Protein 1 homologous protein; and b) measuring the amount of complexes formed in step (a), thereby measuring the homologous protein in said sample.

This invention also provides a method for determining whether a patient is infected with a particular fungus comprising steps of: a) obtaining a sample from the patient; and b) contacting the sample with a panel of antibodies comprising specific antibodies which are capable of binding to *Penicillium marneffei* Antigenic Protein 1 or *Penicillium marneffei* Antigenic Protein 1 homologous protein such that a positive reaction of a specific antibody will indicate that the patient is infected with a particular fungus.

This invention further provides a method of determining whether a compound is capable of binding to *Penicillium marneffei* Antigenic Protein 1 or a *Penicillium marneffei* Antigenic Protein 1 homologous protein comprising steps of: a) linking the said protein onto a matrix; b) contacting the compound with the linked protein under conditions permitting formation of complexes between the compound and the polypeptide; and c) detecting the complexes, wherein a positive detection will indicate that the compound is capable of binding to *Penicillium marneffei* Antigenic Protein 1 or a *Penicillium marneffei* Antigenic Protein 1 homologous protein. In an embodiment of this method, the compound is labeled with a detectable marker.

This invention provides a kit for measuring antibodies against *Penicillium marneffei* Antigenic Protein 1 in a sample comprising in separate compartments: a) the polypeptide of an isolated polypeptide selected from the group consisting of (i) a polypeptide comprising amino acid 1 to amino acid 430 of SEQ ID NO:2, fragments, analogs and derivatives of said polypeptide; and b) a positive control antibody capable of specifically binding to *Penicillium marneffei* Antigenic Protein 1.

This invention also provides a kit for measuring *Penicillium marneffei* Antigenic Protein 1 in a sample comprising in separate compartments: a) the antibody capable of specifically binding to the *Penicillium marneffei* Antigenic Protein 1 homologous protein; and b) a positive control of purified *Penicillium marneffei* Antigenic Protein 1.

These diagnostic kits may based on Enzyme-linked immunsorbent assay (ELISA) or radioimmunoassay (RIA) or other detection technologies known in the art.

This invention provides a method for identifying a gene coding for an immuno-dominant protein of a pathogenic fungus comprising steps of: (a) obtaining hyperimmune serum against the whole fungal cells of the pathogen fungus; (b) contacting said hyperimmune serum with clones of an expression library which contains DNA inserts specific for the pathogen fungus under conditions permitting binding of the expressed insert and said serum; (c) isolating clones capable of binding to said antibody; and (d) determining the DNA sequence of the inserts to identify the genes contained in the clones, wherein the majority of the clones will be coding for the immuno-dominant protein of the pathogenic fungus, thereby determining the gene codes for an immuno-dominant protein of a pathogenic fungus. In an embodiment, the hyperimmune serum is obtained by immunizing guinea pig with the whole fungal cells. Other animals such as rats, mice, or rabbits may be similarly used to produce the hyperimmune serum.

Finally, this invention provides genes identified by the above methods.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37_C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 mg of approximately equimolar amounts of the DNA fragments to be ligated.

Unless otherwise stated, transformation was performed as described by the method of Graham, F. and Van der Eb, A., Virology, 52:456–457 (1973).

EXAMPLE 1

The Cloning of PMAP1 cDNA that Encodes a Highly Antigenic Protein on *Penicillium marneffei*

The *Penicillium marneffei* strain PM4, an isolate from a patient, was used throughout the study. A loopful of yeast colony was used to inoculate 100 ml RPMI medium (Gibco) in 500-ml flask at 37° C. in a gyratory shaker. A 4-day-old-culture was harvested for RNA extraction.

To construct the cDNA expression library, Stratagene's library construction system was used. Briefly, the *Penicil-*

*lium marneffei* yeast phase culture was made as described above. 100 ml 4-day-old yeast cells were collected and resuspended in 5 ml TRIzol reagent (GibcoBRL: total RNA isolation reagent). Disruption of yeast cells required sonication as described above. The homogenized samples were incubated for 15–30 minutes at room temperature with rocking. 1 ml of chloroform was added to 5 ml TRIzol reagent. Vortex tubes vigorously for 1 min and incubate the sample further at room temperature for 5 minute. The sample was centrifuged at 12,000×g for 15 minutes at 4° C. RNA was removed from the upper aqueous phase and extracted once again with equal volume of chloroform. RNA was precipitated by mixing with 0.5 volume of isopropanol. The sample was incubated at room temperature for 10 minutes and centrifuged at 12,000×g for 10 min at 4° C. The RNA pellet was washed with 75% ethanol and centrifuged at 7,500×g for 5 minutes at 4° C. Dried RNA was dissolved in DEPC-treated water, measured at $OD_{260}$, aliquoted and stored at −80° C.

Poly(A)$^+$ RNA was obtained by using QuickPrep Micro mRNA purification kit (Pharmacia) basing on conventional oligo(dT) cellulose method. Briefly, the RNA sample was mixed with oligo (dT) cellulose resin in guanidinium thiocyanate. Then, the oligo (dT) cellulose washed with high salt buffer [10 mM Tris-HCl (pH 7.5), 1 mM EDTA, 0.5 M NaCl], followed by low salt buffer [10 mM Tris-HCl (pH 7.5), 1 mM EDTA, 0.1 M NaCl]. Poly (A)$^+$ RNA was eluted with TE buffer [10 mM Tris-HCl (pH 7.5), 1 mM EDTA]. The mRNA was then used for the construction of 1-ZAP cDNA expression library (Stratagene, Inc.).

To produce antibody from Guinea pig for the screening the Lambda expression library, yeast cells from a 4-day-old-culture were washed 3 times in PBS and finally suspended in PBS at turbidity of McFarland standard greater or equal to 3 containing 0.05% phenol. 500 ul of yeast suspension was mixed thoroughly with equal part of complete Freud's adjuvant and injected intramuscularly into the animal's thigh. Incomplete Freud's adjuvant was used in subsequent immunization and a total of 4 inoculations were required to complete the program in 2 months.

Approximately 50,000 plaques from the *Penicillium marneffei* yeast cDNA library were plated and used for screening (Molecular Cloning, Sambrook et al., 1989. Cold Spring Harbor Lab. Press). Nitrocellulose membranes (NC) prewetted with filter-steriled 10 mM IPTG were layered on top of the plates and incubated at 37° C. for another 4 hours. The NC membranes were removed and rinsed briefly in PBS buffer, and stored dried at 4° C. The membranes were blocked in 5% BSA and incubated with 1:500 dilution of immunized guinea pig serum, washed and developed as immunoblots described above. Autoradiographs for membranes were scrutinized for plaques to which the proteins expressed were recognized by the immune serum. Ten putative clones were found and the cDNA inserts were excised by using ExAssist helper phage, XL-1 Blue and SOLR *E. coli* (Stratagene, Inc.), yielding pBluescript SK(-) containing inserts.

The ten putative clones carried in SOLR *E. coli* cells were induced by 2 mM IPTG, cellular lysates were extracted and electrophoresed in 10% SDS-polyacrylamide gels. The protein gels were electro-transferred onto NC membranes and reacted with sera from preimmunized and immunized guinea pig serum (1:1000), *Penicillium marneffei* infected patients and normal control patient (1:500). Six clones produced prominent band at about 50 kd position in both immunized Guinea pig serum and *Penicillium marneffei* infected-patient serum but absent in preimmune serum and normal patient control serum. Further sequence analysis revealed that all six clones contain the same gene, hereby named *Penicillium marneffei* Antigenic Protein 1 (PMAP1).

EXAMPLE 2

Sequence Analysis of Penicillium Gene and Identification of the Full Coding Sequence of the Polypeptide Clone PMC10 that contains the longest insert (1.5 Kb) was sequenced. Multiple nested "unidirectional" deleted clones extending progressively from one end the other were produced from clone PMC10. Briefly, the cDNA insert was cleaved from the PBluescript vector by double digestion with restriction enzyme Bam H1 and Kpn1 (no internal restriction site in the insert) (GibcoBRL). Double stranded nested deletion reaction was carried out by digestion with Exonuclease III and S1 nuclease (Double Stranded Nested Deletion Kit, Pharmacia), different sized deletions were obtained in different time points and assayed by agarose gel electrophoresis. The deleted inserts were religated and transformed into M1061 *E. coli*.

The entire sequence was determined by using the universal M13F, M13R primers with DNA sequenase version 2.0 (United States Biochemicals, Inc.). High fidelity of the sequencing result was achieved by having sequenced at least two clones covering the same region. The sequence was assembled and analyzed by the GCG 8.0 package (Genetics Computer Group, Inc.).

The result of the sequence analysis is shown in FIG. 1. The PMAP1 gene contains an open reading frame of 462 amino acid residues. BLAST analysis was performed using NCBI programs in order to search for potential homologues that might implicate the potential functions of PMAP1. The BLAST search results indicated that PMAP1 was a novel gene. In addition, BLAST analysis revealed that PMAP1 did not have any significant homologue in all public data bases. However, careful examination of PMAP1 protein sequence revealed sequence features that are common for fungal cell wall proteins including several cell wall proteins of *Saccharomyces cerevisiae* shown in FIG. 2 (Van Der Vaart et al. 1995. J. Bacteriol. 177:3104–3110) of *Candida albicans* (Bailey D. A. et al. 1996. Bacteriol 178: 5353–5360). PMAP1 has a putative N-terminal signal sequence (underlined/black boxes at N-terminal) found on most secretary proteins (von Heijne, G., 1986. Nucleic Acid Res. 14:4683–4690), a putative C-terminal glycosylphosphatidylinositol (GPI) domain (underlined/black boxes at C-terminal), and a serine- and threonine-rich region (italic/shaded boxes). GPI domain is utilized for many proteins to anchor to eukaryotic cell membrane (Udenfriend, S. 1995. Annu. Rev. Biochem. 64:563–591). Once anchored on to the cell membrane, the cell surface proteins can play many important physiological functions, including cell-cell recognition, cell adhesion, receptors and nutrient and ion transporters. After processing, the matured PMAP1 protein has 411 amino acid residues with a molecular weight of 43 kd for the protein portion alone. PMAP1 is expected to be N-glycosylated at asparagine residues, including the last residue that is to be GPI anchored, similar to that of other members of the yeast cell wall proteins. In addition, PMAP1 contains a 77 amino acids stretch of serine/threonine rich region at its C-terminal half, indicating that the protein should also be O-glycosylated.

EXAMPLE 3

In Vitro Translation of the PMAP1 Gene and Immunoprecipitation of the Protein by Immunized Animal Serum The PMAP1 protein was expressed by TNT™ Coupled Reticulocyte Lysate System (Promega, Inc.). Briefly, the reaction was set up with 1 ug of pBSK-PMAP1 plasmid, 4 ul of $^{35}$S-methionine (1,000 Ci/mmole at 10 mCi/ml), reaction buffer, amino acid mixture minus methionine, RNA polymerase T3 and 25 ul of rabbit reticulocyte lysate. The reaction was incubated at 30° C. for two hours. 0.5 ul of the in vitro translated protein was then analyzed on a 10% SDS-PAGE gel shown in FIG. 3.

For immuniprecipitation, 5 ul of the in vitro translated protein was added into 300 ul of lysis buffer containing 50 mM Tris-HCl, pH 7.4, 250 mM NaCl, 0.1 % NP40, 5 mM EDTA, 2 ug/ul BSA. 1 ul of each pre-immunized or immunized Guinea pig sera as primary antibodies were added to separated tubes. The incubation was carried out at 4° C. for one hour. Then, 50 ul of 50% Protein G Sepharose (Pharmacia Biotech) was added to the mixture for a further incubation of one hour at 4° C. with on a rocker for constant mixing. The immunocomplex was then pelleted in a microcentrifuge at 4° C. for 5 second and washed four times with 1 ml of lysis buffer each. After the final wash, the pellet was resuspended into 25 ul of 2×SDS sample buffer and heated to 95° C. for five minutes. 20 ul of the final sample was loaded onto a 10% SDS-PAGE gel. After running, the gel was fixed and then soaked in Amplify™ for 30 minutes (Amersham, Inc.), after which the gel was dried on a Bio-Rad Gel Dryer (BioRad, Inc.). The exposure was done with a Kodak XAR film with intensifying screen overnight at −80° C.

Figure 3:
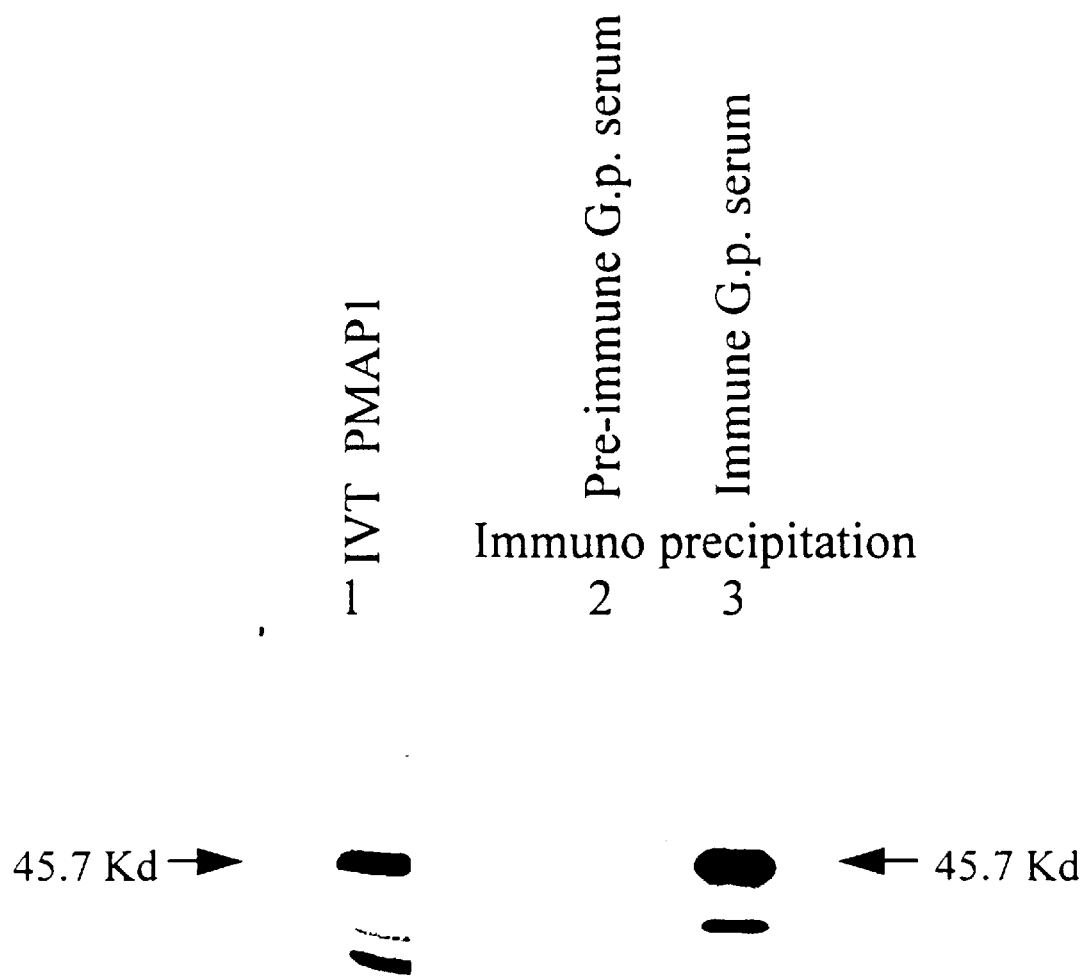
FIG. 3 depicts a photograph of a gel after in vitro transcription, translation and SDS-PAGE gel electrophoresis separation of the polypeptide of the present invention. The in vitro translated protein can be specifically recognized by immunized animal serum but not pre-immunized serum through immunoprecipitation assay.

The in vitro translation of PMAP1 gene produces an polypeptide of 50 kd shown in FIG. 3, consistent with the predicted open reading frame of the PMAP1 gene sequence. Other minor fragments are the products of the internal translation initiations.

EXAMPLE 4

Figure 4:
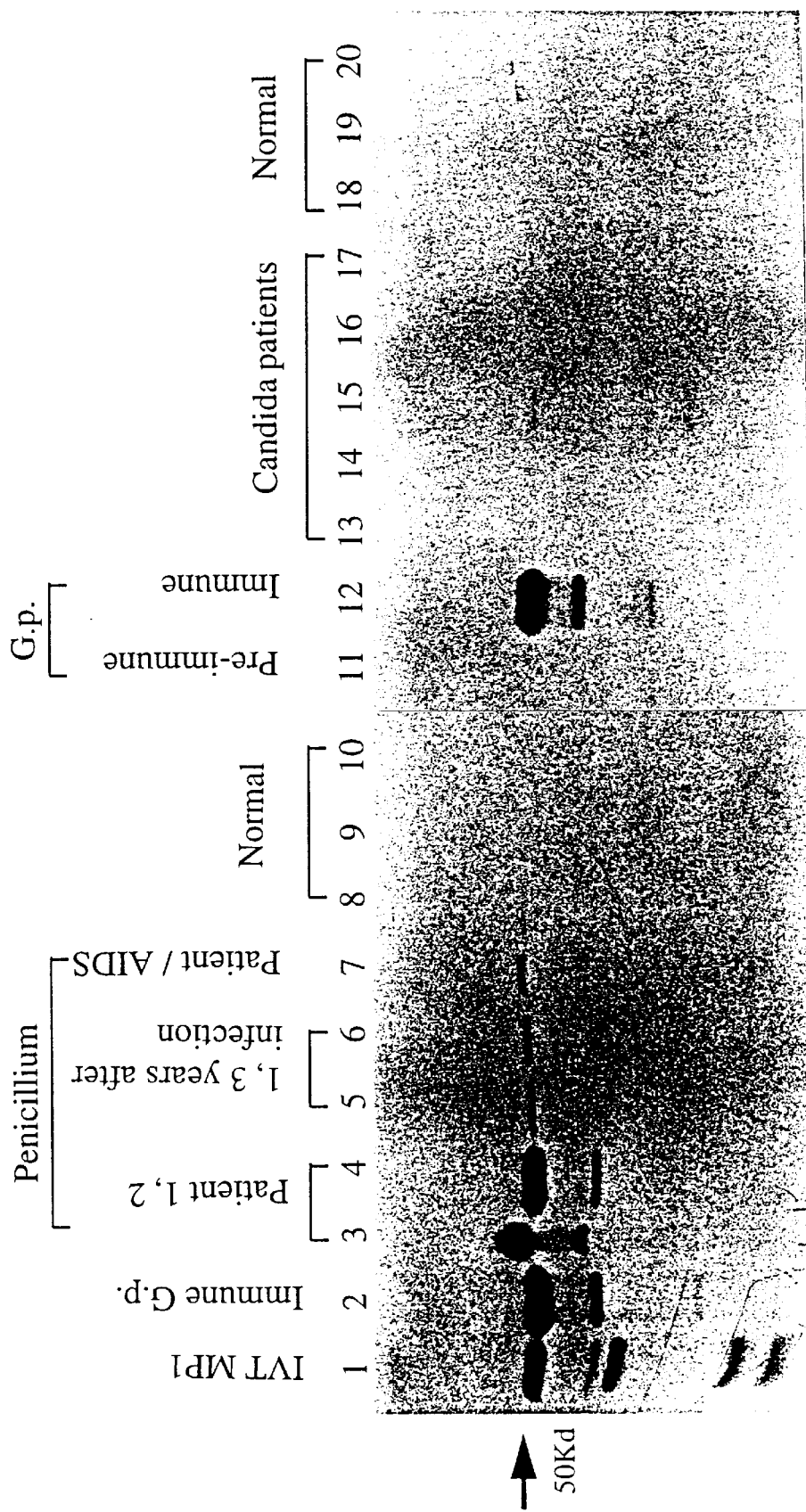
FIG. 4. depicts that the protein produced in vitro can be recognized specifically by sera from patients that have current infection of *Penicillium marneffei*, but not from sera taken from patients with a different type of systemic infection by *Candida albicans*.

Specific Recognition of PMAP1 Protein by Sera from Penicillium Infected Patients The experiments were done similar to that of Example 3. The results are also shown in FIG. 4. Two *Penicillium marneffei* patients' sera were collected during the first admission to Queen Mary Hospital, Hong Kong (Lane 3, 4). They were free from HIV infection, and had persistent fever not responsive to antibiotic treatments prior to admission. At Queen Mary Hospital, they were diagnosed through invasive bone marrow and spleen biopsies to have systemic fungal infection by *Penicillium marneffei*. Two previous patients were recalled back to the hospital for blood testing one and three years after recovered from the original Penicillium infection (Lane 5, 6). Blood of one HIV positive patient that having ongoing Penicillium infection was also collected (Lane 7). Normal controls were blood samples from the hospital staffs that had no history of this fungal infection (Lane 8, 9, 10).

The results show that the patients' sera contained very high levels of anti-PMAP1 antibodies, similar to that of the immunized animal. One year after the infection, there is a marked reduction of the specific antibody level against this protein. The AIDS/Penicillium patient serum shows a somewhat lower level of specific antibody but yet significant higher than that of the normal controls. This result is in consistent with the immunofluorescence result that was obtained earlier showing that while the sera from Penicillium patients showed average titer of about 1000, the AIDS/Penicillium patients showed average titer of 200 to 400. The normal controls had titers of less than 50 (Lancet 1994, 344, 444–5). The results of this invention indicate that normal control sera do not immunoprecipitate the labeled PMAP1 protein.

EXAMPLE 5

Absence of Immune Cross Reactivity Against PMAP1 Protein from Sera of Other Fungal Infected Patients The experiments were done similar to that of Example 3 and the results are shown in FIG. 4. First, the PMAP1 protein was produced by in vitro translation; then, the protein was immunoprecipitated with a panel of antibodies, including the ones from other systemic fungal infected patients at Queen Mary Hospital. Sera from five systemic *Candida albicans* infected patients that were HIV seronegative were chosen for the study to determine the specificity of the serological test using PMAP1 protein.

Lane 3 to 7 show no detectable immunoprecipitated band, indicating that the Candida patients' sera do not recognize the PMAP1 protein, therefore, no sera-cross reactivity can be observed. Lane 8, 9, 10 are three other normal control sera of different people from those of Example 4. Again, normal people contain no detectable levels of antibody against this fungal protein.

EXAMPLE 6

Construction of Recombinant Plasmid to Produce GST-PMAP1 Fusion Protein

Figure 5:
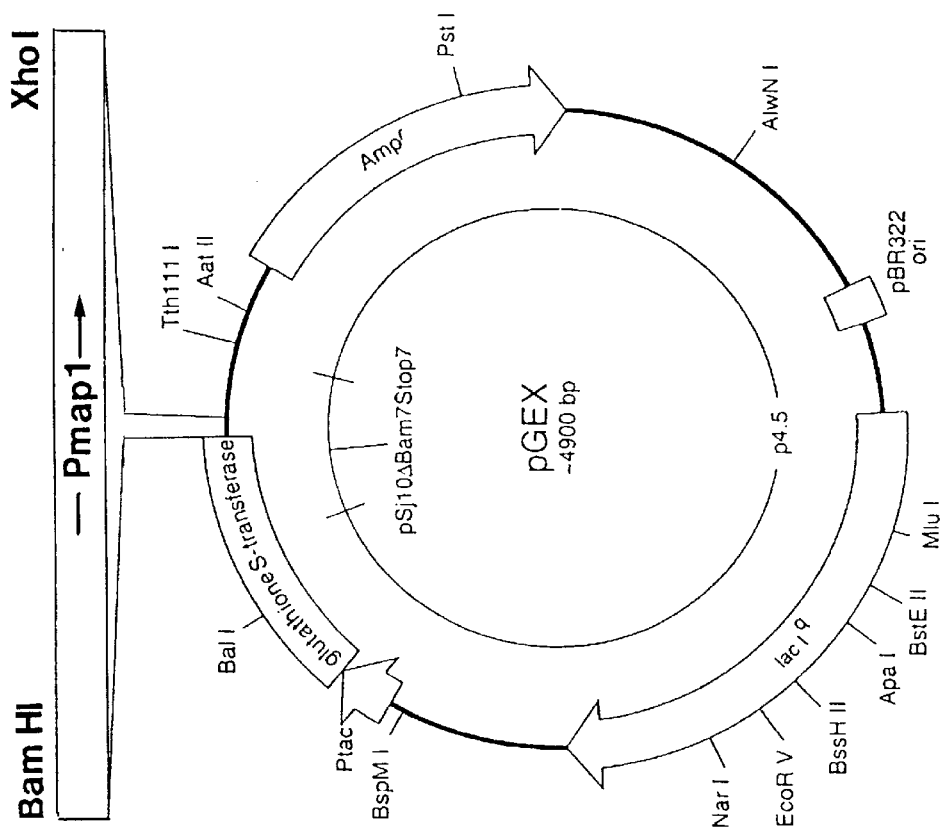
FIG. 5. depicts the map of an expression plasmid construct that contains PMAP1 fused in frame with glutathione S-transferase allowing the expression and purification of GST-PMAP1 fusion protein.

To produce the fusion plasmid for protein purification, primers were used for the amplification of PMAP1 gene from PBSK-PMAP1 plasmid. Amino acid residues 35 to 462 of PMAP1 were amplified and cloned into Bam HI and Xho I sites of pGEX30X expression vector in frame and downstream of glutathione S-transferase. The map of such a plasmid is shown in FIG. 5.

EXAMPLE 7

Expression and Purification of Recombinant PMAP1 Protein in *E.coli*

Figure 6:
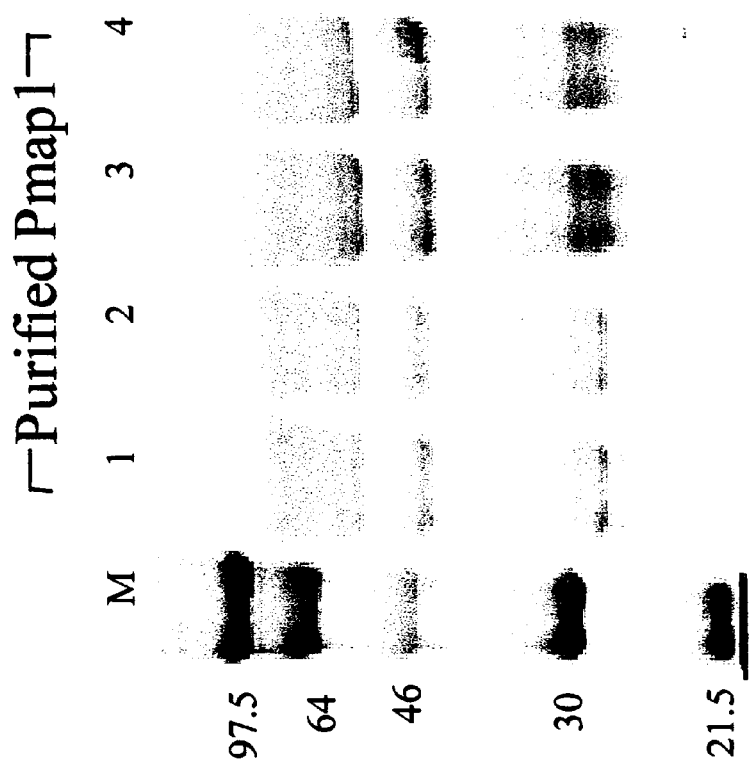
FIG. 6. depicts photographs of recombinant PMAP1-GST fusion protein produced and purified from *E.coli* bacterial cell. The purified PMAP1 fusion protein can be specifically recognized by Guinea pig immune serum against the killed *P. marneffei* cells.

*E.coli* cell carrying GST-PMAP1 plasmid was induced with 1 mM IPTG to express the fusion protein. The GST-PMAP1p fusion protein was expressed and purified as described by GST Gene Fusion System (Pharmacia Biotech). 10 to 15 mg protein was routinely obtained from 1 liter of *E.coli* cells carrying the fusion plasmid. The purified fusion protein was separated on SDS gel followed by Coomassie blue staining. The GST-PMAP1p is probably very unstable in *E.coli* since multiple protein bands were detected even with minimal induction time (1 hr) in a protease deficient strain BL21. After purification, several bands can be seen on SDS gel with the largest one being 75 kd shown in lane 1 through lane 4 of FIG. 6, consistent with the expected molecular weight for the fusion protein of 73 kd. To confirm the purified fusion protein as GST-PMAP1p, Western blot analysis of the purified fusion protein was carried out using serum from Guinea pig that was immunized by killed *P. marneffei* cells. The results indicated the purified proteins are highly reactive to the Guinea pig immune serum against the killed *P. marneffei* cells (results not shown).

EXAMPLE 8

Production of Anti-PMAP1 Specific Antibodies

To produce the antibody from Guinea pig for the screening the 1 expression library, yeast cells from a 4-day-old-culture were washed 3 times in PBS and finally suspended in PBS at turbidity of McFarland standard ( 3 containing 0.05% phenol. 500 (1 yeast suspension was mixed thoroughly with equal part of complete Freud's adjuvant and injected intramuscularly into the animal's thigh. Incomplete Freud's adjuvant was used in subsequent immunization and a total of 4 inoculations were required to complete the program in 2 months.

To produce specific antibodies against PMAP1p, 500 ug/250 ug of GST-PMAP1p recombinant protein was mixed with equal parts of complete Freud's adjuvant and injected subcutaneously into two rabbits and three Guinea pigs. Incomplete Freud's adjuvant was used in subsequent injections. Serum was taken two weeks after the third injections.

EXAMPLE 9

PMAP1 is Specifically Located in the Cell Wall of *P. marneffei* Yeast Cells

Figure 7:
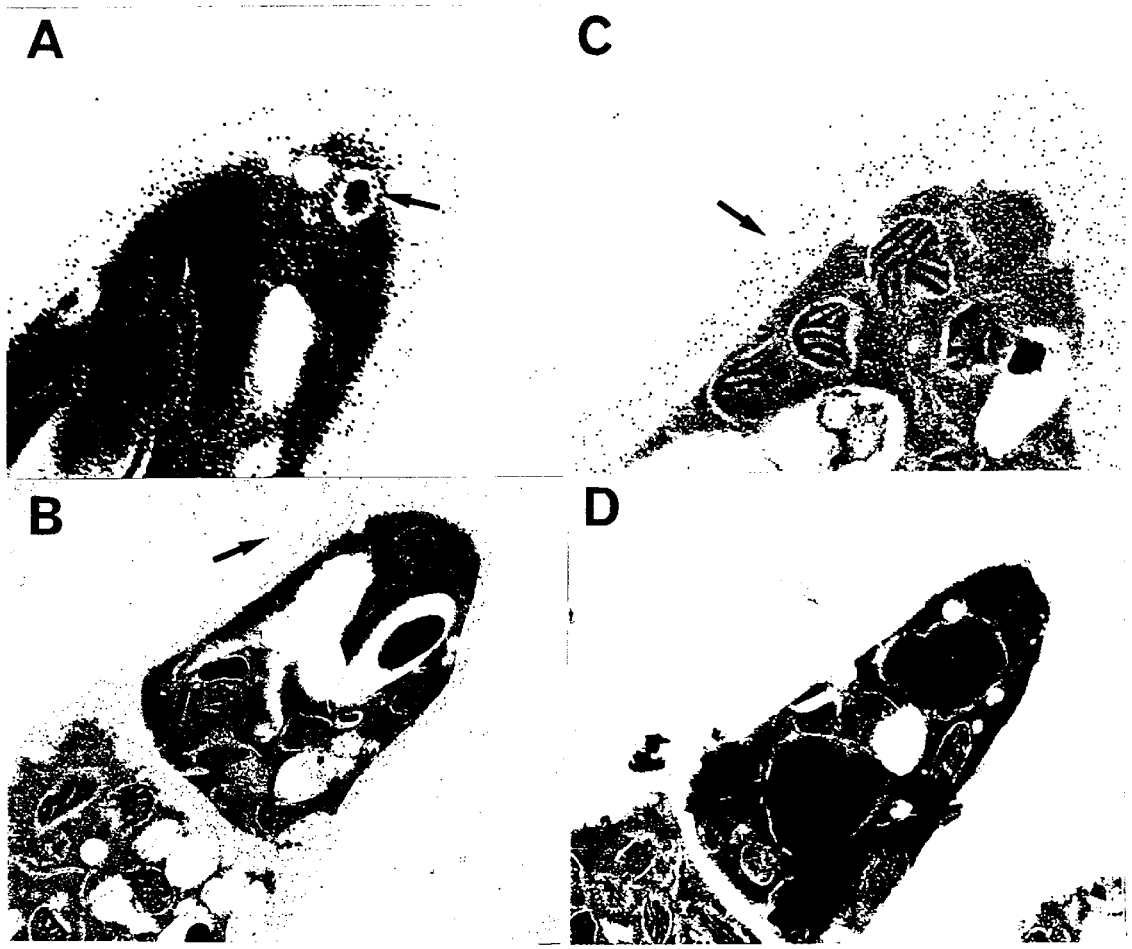
FIG. 7. depicts the photographs indicating that PMAP1 is specifically located in the yeast cell wall of *P. marneffei* using immunogold staining under electron microscope.

Immuno-gold staining of *P. marneffei* cells with anti-PMAP1 antibody was carried and the electron microscopic results are shown in FIG. 7. (A, B, C) Staining of *P. marneffei* yeast cells with specific rabbit anti-PMAP1 antibody. The protein is specifically located in the yeast cell wall throughout the entire cell including septum. The protein cover the whole thickness of the cell wall. It appears that the protein is contained in the vesicles before release through the cell membrane to the cell wall as indicated (A). In addition, the PMAP1p appears to be release from the cell wall as pointed (B), suggesting that this protein are being shaded from the cell. (D) Negative control staining of *P. marneffei* cells revealed no specific staining o the cell.

EXAMPLE 10

A Antibody Detection Test for Anti-PMAP1 Antibodies

| Pmap1 Antibody Test | | |
|---|---|---|
| Coating Buffer | For 1L | pH 9.6 |
| | Na$_2$CO$_3$ | 1.5 g |
| | NaHCO$_3$ | 2.93 g |
| Blocking Buffer | 2% BSA/PBS | pH 7.4 |
| Wash Buffer | PBS/0.05% Tween 20 | pH 7.4. |
| Substrate Buffer | For 1L | pH 5.0 |
| | Citrate Acid H$_2$O | 7.3 g |
| | Na$_2$HPO$_4$ 12H$_2$O | 23.88 g |

Plates were coated the night before, 1:2000 dilution of PMAP1 protein (10 mg/ml) in Coating Buffer, 4 (C O/N.
Wash plate 2 times with Wash Buffer.
Block plate with Blocking Buffer, 100(1/well. Incubate 37(C. for 1 hour.
Dilute serum sample 1:200 & 1:400 in Blocking Buffer.
Add 100(1 of diluted sample into each well. Incubate in 37(C. for 1 hour.
Wash plate 4 times with Wash Buffer.
Dilute conjugate 1:7000 in Blocking Buffer.
Add 100(1 of diluted conjugate into each well. Incubate in 37(C. for 1 hour.
Dissolve 4 OPD tablets into 12 ml of Substrate Buffer.
Before use, add 5(1 of 30% H$_2$O$_2$ into above mix.
Wash plate 4 times as above.
Add 100(1 of above substrate mix into each well.
Develop in 37(C. till signal appears, or for 30 minute.
Stop reaction by adding 25(1 of 2M H$_2$SO$_4$ into each well.
Read OD as soon as possible.
Measurement Filter 492 nm
Reference Filter 405 nm

EXAMPLE 11

Figure 8:
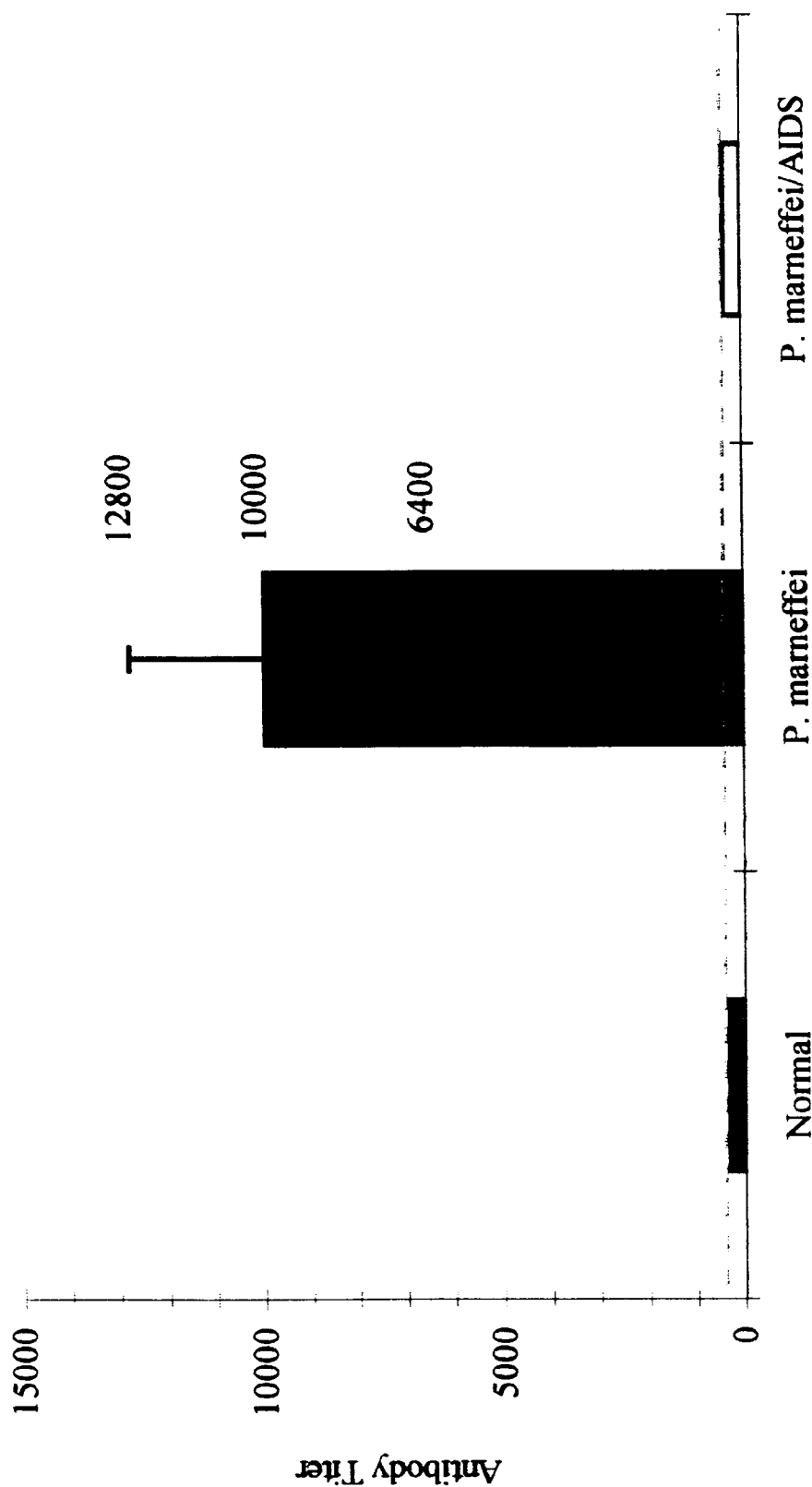
FIG. 8. depicts the detection of specific antibodies in *P. marneffei* patients with an ELISA based serological test using purified recombinant PMAP1 protein.

Detection of the Presence of Specific Antibodies Against PMAP1 Protein in *P. marneffei* Infected Patients An evaluation of the ELISA test for the presence of anti-PMAP1 antibody is shown in FIG. 8. The numbers used for the evaluation are: 1) 100 blood donors as normal control; 2) two specimens from *P. marneffei* immunocompetent patients; 3) nine specimens from *P. marneffei* patients who were also diagnosed AIDS. Antibodies titer were the reverse of the largest dilution where the OD readings were still no less then 1.0.

The results shown in FIG. 8 indicated that high level of specific antibodies against PMAP1 were detected in *P. marneffei* patients who were immunocompetent.
The anti-PMAP1 antibody levels were drastically reduced in AIDS/*P. marneffei* patients.

EXAMPLE 12

Antigen Detection Test for the Detection of PMAP1 Protein

| PMAP1 Antigen Test | | |
|---|---|---|
| Coating Buffer | For 1L | pH 9.6 |
| | Na$_2$CO$_3$ | 1.5 g |
| | NaHCO$_3$ 2.93 g | 2.93 g |
| Blocking Buffer | 2% BSA/PBS | pH 7.4 |
| Wash Buffer | PBS/0.05% Tween 20 | pH 7.4 |
| Substrate Buffer | For 1L | pH 9.8 |
| | Glycine | 7.51 g |
| | MgCl$_2$ | 203 mg |
| | ZnCl$_2$ | 136 mg |

Coat plate with guinea pig anti-PMAP antibody (1:5000)in Coating Buffer 100(1/well, O/N at 4(C.
Wash plates 2 times with Washing Buffer.
Block plates with 100(1/well of Blocking Buffer. Incubate for 1 hr in 37(C.
Diluted PMAP protein standard and samples in Blocking Buffer. Incubate for 1 hr in 37(C.
Wash plates 4 times with Washing Buffer.
Dilute Rabbit anti-PMAP (1:500) in Blocking Buffer, add 100(1/well. Incubate for 1 hr in 37(C.
Wash plates 4 times as above.
Dilute goat anti-rabbit alkaline phosphatase conjugate 1:2000 in Blocking Buffer, add 100(1/well.
Incubate for 1 hr in 37(C.
Wash plates 4 times as above.
Dissolve 2 p-Nitrophenyl Phosphate (pNPP) tablets in 10 ml of Substrate buffer.
Add 100(1/well, incubate in 37(C. till color develop.
Stop by adding 25(1/well 3N NaOH into each well.
Read OD at 405 nm as soon as possible.

EXAMPLE 13

Detection of the Presence of Specific PMAP1 Protein Antigen in *P. marneffei* Cell Culture Medium

Figure 9:
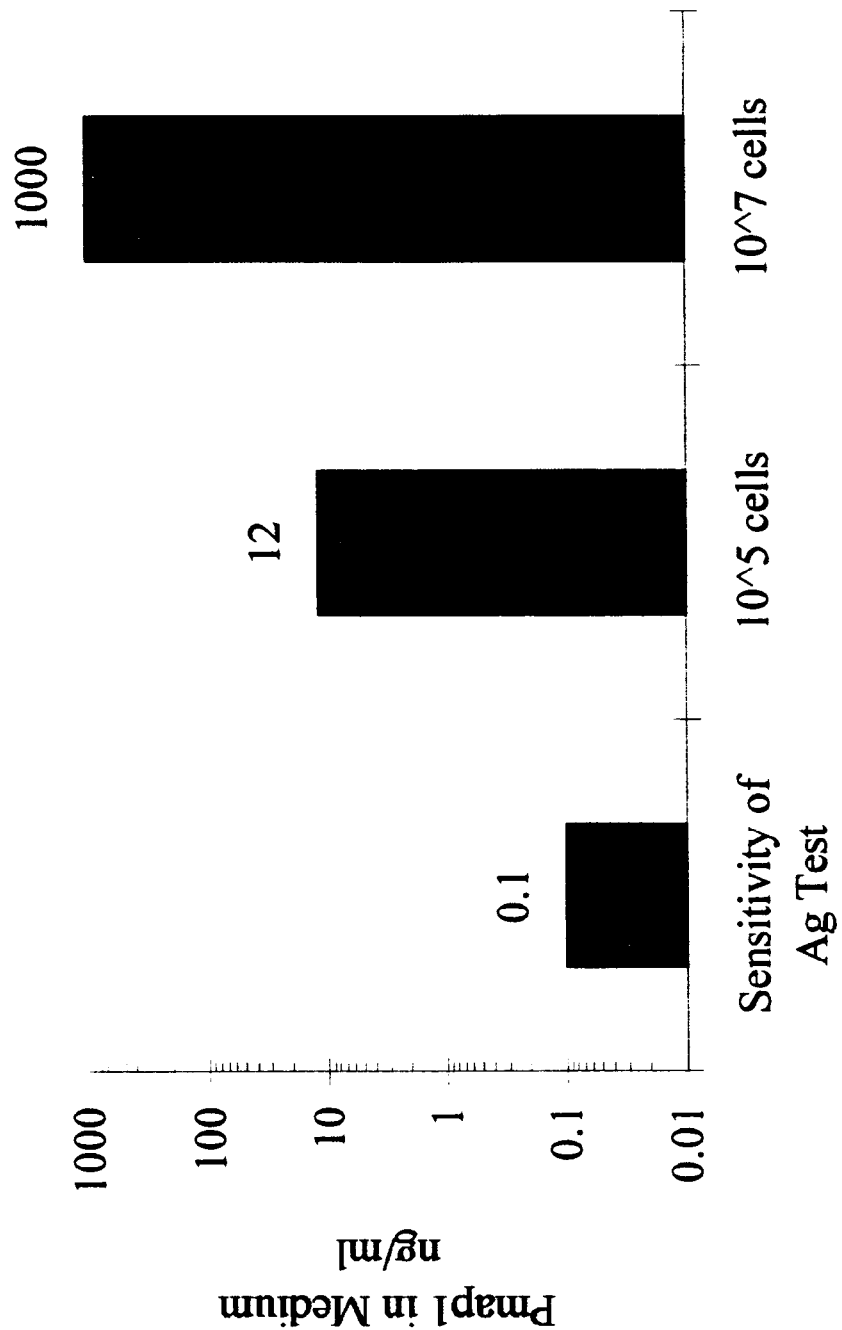
FIG. 9. depicts the detection of PMAP1 protein in *P. marneffei* cell culture media with an ELISA based antigen test for PMAP1 antigen using specific antibodies against PMAP1 recombinant protein.

*P. marneffei* cell cultures were obtained and the cell numbers were counted under miscroscope. The media were harvested and filtered through a 0.45 um filter to remove all living yeast cells. An ELISA test was performed with the media based on the description of Example 12. The standard curve was established in the same experiment with the purified recombinant PMAP1 protein that has been quantitated based on Bradford Assay (Bio-Rad, Inc.). The result of the study is shown in FIG. 9.

The sensitive of the PMAP1 antigen test is 10 pg/test or 100 pg/ml for the stock solution where 100 ul was used for each wall on ELISA plates. The culture media from $1\times10^7$ cells contain approximately 1 ug/ml of PMAP1 protein, or about 1,000 greater than the minimal sensitivity of the test. The result indicated that PMAP1 protein was shed into the culture media in large quantities.

EXAMPLE 14

Figure 10:
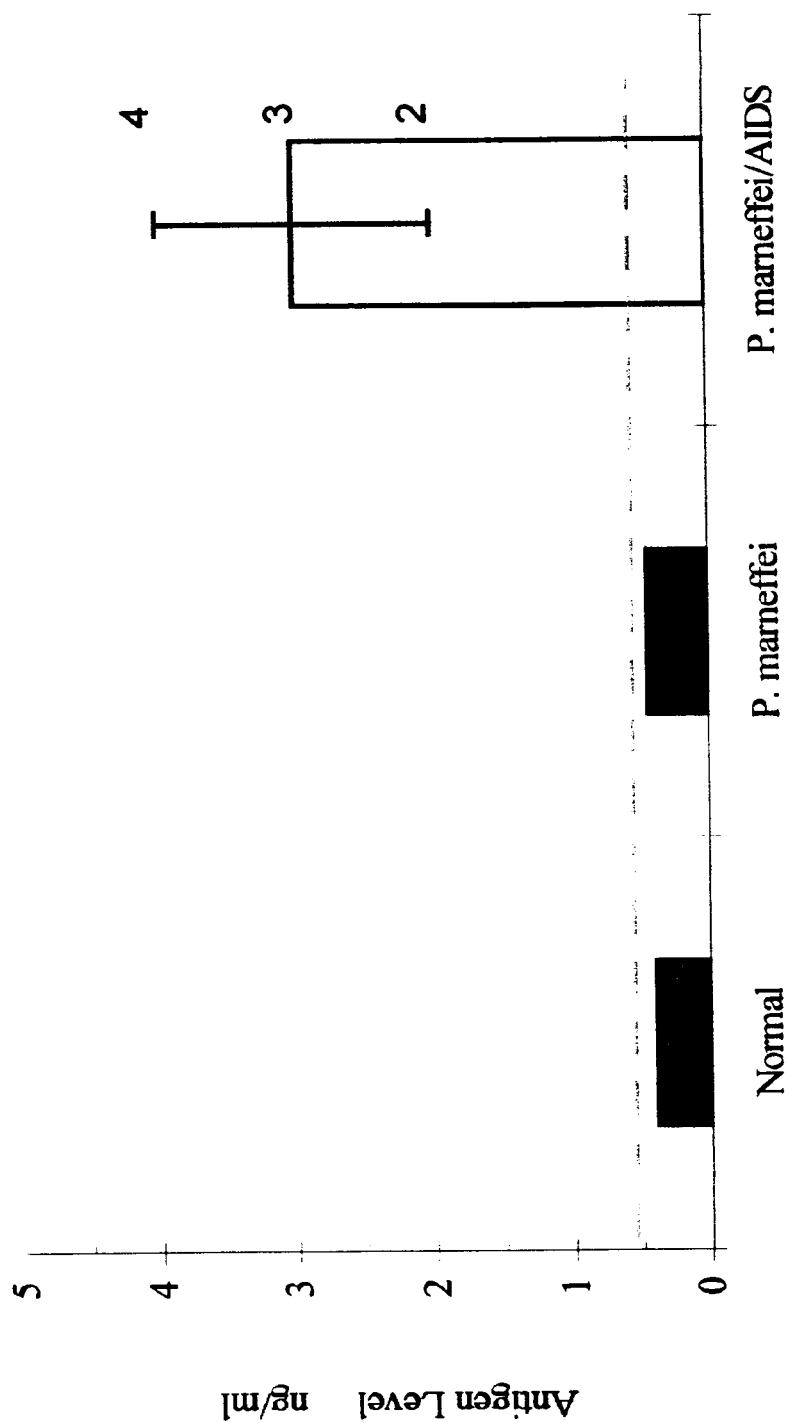
FIG. 10. depicts that PMAP1 protein antigen can be detected specifically from urine and serum samples of documented *P. marneffei* patients who are immunocompromised.
Figure 11:
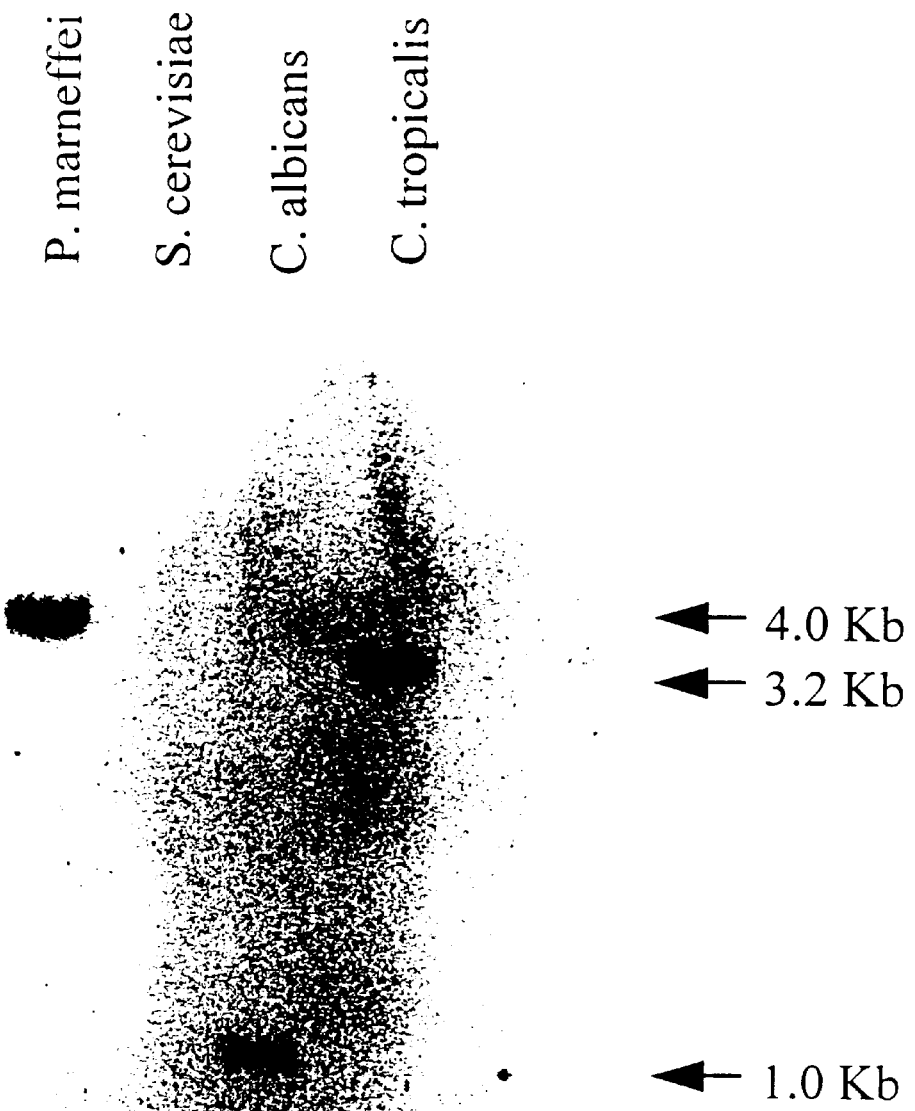
FIG. 11 depicts the detection of putative PMAP1 homologous genes in both pathogenic fungi, *Candida albicans* and *Candida tropicalis*, by low stringency hybridization of fungal genomic DNA using labeled PMAP1 DNA probe. A non-pathogenic fungus, *Saccharomyces cerevisiae*, failed to reveal any positive hybridization signal.

Detection of the Presence of Specific PMAP1 Protein Antigen in *P. marneffei* Infected Patients A clinical evaluation of the ELISA test for the presence of anti-PMAP1 antibody is shown in FIG. 10. The numbers used for the evaluation are: 1) 100 blood donors as normal control; 2) two specimens from *P. marneffei* immunocompetent patients; 3) nine specimens from *P. marneffei* patients who were also diagnosed AIDS. To determine the exact levels of PMAP1 protein in patients sera, a standard curve was established in the same experiment similar to that described in Example 13.

The test allows the detection of circulating PMAP1 protein antigen in *P. marneffei* infected AIDS patients at a concentration of 3 ug/ml, approximately 6 time high than the limit of the sensitivity. The test is specific with not a single positive sera from 100 normal blood donors at Queen Mary Hospital in Hong Kong.

EXAMPLE 15

Low Stringency Hybridization to Examine Putative PMAP1 Homologous in Pathogenic Candida Strains Fungal strains, *Penicillium marneffei, Saccharomyces cerevisiae, Candida albicans*, and *Candida tropicalis* were grown in Sabouraud media. The cells were harvested and treated with lyticase (Sigma, Inc.) to remove the cell wall. Genomic DNA isolation was done using GENOME™DNA kit from Bio 101 Inc. Approximately 10 ug of genomic DNA was digested with 20 u of EcoRI enzyme and was separated on 1% agarose gel. The DNA was then transferred onto Hybond-N membrane (Amersham Inc.)

The full length PMAP1 radioactive probe was produced using Prime-It II (Stratagene, Inc.). The hybridization was carried out at low stringency condition. An example of the condition of hybridization is to incubate the labeled probes with the libraries overnight at 42° C. in a hybridization solution containing 5×SSC, 35% formamide, 5×Denhardts'; solution, 250 ug/ml carrier DNA, 50 mM NaPO4 and 1% SDS. Washes were done with 1×SSC, 0.1% SDS for twice at room temperature and twice at 37° C. The membrane was then exposed with Kodak XAR5 film at −80° C. with intensifying screen for two days.

The results indicate that single bands of 4.0, 3.2 and 1.0 from *Penicillium marneffei, Candida albicans* and *Candida tropicalis* can be detected specifically with PMAP1 DNA probe. Both *Candida albicans* and *Candida tropicalis* are two of the most prevalent fungal pathogens involved with systemic fungal infection in human. They have only the yeast form in their life cycle, similar to that of yeast *Saccharomyces cerevisiae*. On the other hand, the non-pathogenic yeast strain, *Saccharomyces cerevisiae*, failed to reveal any specific hybridization band.

What is claimed is:

1. An isolated polynucleotide comprising a member selected from the group consisting of:

(a) a polynucleotide of at most 1539 nuleotides encoding the polypeptide as set forth in SEQ ID NO:2;

(b) a polynucleotide capable of selectively hybridizing to the polynucleotide of (a); and (c) a polynucleotide comprising a nucleotide sequence fully complementary to the polynucleotide of (a) or (b).

2. The isolated polynucleotide of claim 1, wherein said member is (a).

3. The isolated polynucleotide of claim 2, wherein said member is (a) and the polypeptide comprises amino acid 1 to 430 of SEQ ID NO.2.

4. The isolated polynucleotide of claim 1, wherein the polynucleotide is DNA.

5. A method of making a recombinant vector comprising inserting the isolated polynucleotide of claim 2 into a vector, wherein said polynucleotide is DNA.

6. A recombinant host cell comprising the polynucleotide of claim 2, wherein said polynucleotide is DNA.

7. A method for producing a polypeptide compromising expressing from the recombinant cells of claim 6 the polypeptide encoded by said polynucleotide and isolated said polypeptide.

8. A process for producing a polypeptide comprising:

expressing from a recombinant cell containing the polynucleotide of claim 4 the polypeptide encoded by said polynucleotide and isolating said polypeptide.

9. A method of identifying *Penicillium marneffei* Antigenic Protein 1 (SEQ ID NO.:2) homologous genes from a fungus other than *Penicillium marneffei* comprising steps of:

a) obtaining a DNA library containing clones having inserts specific for a fungus other than *Penicillium marneffei*;

b) hybridizing the clones in the library with at least one specific probe for *Penicillium marneffei* Antigenic Protein 1 gene under conditions permitting hybridization of the specific probe to a *Penicillium marneffei* Antigenic Protein 1 homologous gene; and c) isolating clones hybridizing to the probe;

d) determining the DNA sequence of the inserts;

e) comparing the homology in sequence between the *Penicillium marneffei* Antigenic Protein 1 gene and the inserts to confirm the identity of the homologous gene.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1549 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GGCACGAGCG TTAATCAACA TGAAGTTCTT ATCCTCCCTC GTCGTCCTCG GTCTTTCTGC      60

CCAGGCTCTT GCAAGCCCTT ACGTTGATCA CCAGGCTACC AAGGACCAGC GTGATGTAAA     120

TGTTTTCAAG CAGGTCCTCC AAGATATTAA CCTCGATGTG CAGAAATTCG ACCAGGATAT     180

CACTCAATAC CAGGGCGGTG ATCCCACAGT CCTTCTCGCT GACTCTGATG CTATTATCAA     240

AACCACTGAG GAAGGCATTC AGAGAATCGG ACCTCAGCCT CCCCTTAGTG TCACTGAGGC     300

CCTTGCCCTT GTTGGCCCTG TTCAGGGTGT AAACAAGTTG ATTATGAAGG CTGTCGATCA     360

CCTTATTGAA AAGAAGGGTC CTCTTGTTGG TGGGGGTTAT GGTCCTCAAG TCAAGGATAG     420

TCTTGAGAGG CAGGCCCATG CTGCGAGTAA ACTCAGCGAG TTAGTCTCCT CAAAGGTCCC     480

TAGTCCACTC GCCCCAATTT CCAAACAGCT CTCCGATCAG GTCGCCCAAG CCCTCCAGAA     540

AGGTATCCAA GCCTTCTCCA TTAGCGCTCG CCAGGCCACC AAGGTAAAGC GTGAGGCCAC     600

CAAGGTCCAG CGTGATATTT CTGCTTTCAA GAAGGTCATC CAGAATATTA GCTTGGCTGT     660

GAACAAGTTT AATGTTGATA TTGAGCGTTA CGTGGGCGGT GATGCTTCTC ATCTTCTCGC     720

TGACGGTAAT GTACTTATCA AAGCTACTCT GGACGGCGTT CAGTCCCTCC AAAATGAGCC     780

TCCGCTTAGC TCCATGGAAG CCCTTGCCCT TGTTGGCCCT GTTCAGGATT TAAGCAATCA     840
```

```
AATCCTACTA GCTATTCAGA ATCTTATTGA TAAGAAGGAA CCTCTTGTTC AGGCTGGTTT      900

TGGTGGTAAA GTCGAGAACA ATCTTAGGCA ACAGGAGGAG GCTGCCCAAA AACTCAGCGA      960

ATTGGTCTCC ACAAAGGTCC CCACGAACT CGCCGACATT TCCCGACAGC TCTCCGATGG      1020

TATCGCTGCT GGCATCAAGA AAGGTATTGA TGCCTTCGCC GGCACTGGCC CCGCCCCAC      1080

TACCAGTAGT ACCCCCGAAG CCTCTACTGC TCCTGCTCCC TCCACTCCTC CTCAGACGCC     1140

TGAAGACACT CTTGTTCCTG CCACATCTAC TCCTGCTCCT GGTCCCGCTC CCACTGCTCC     1200

TGATTCTTCC ATGGTCTGGC CTACCTCTAC CACTGCCTCT CCCGATGTGC AGCCTACCAT     1260

CACCAGCTCT GGCACTTCGG TTCCTGCCGC GCCAACTGGC GGTAATTCTT CGCCCGCCGT     1320

CCCTGCTTTC ACTGGTGCTG CCAGCGCTAA CCAGGTCAGC GGCGCGGTTG GTCTTGCTGC     1380

CGGTCTCCTT GCTGTCCTTG CCTTTTAAAT TCACTTTAAA GTAAACAGCA TACATGAGAA     1440

ATGGGGTTTT TGTTTCTGC TTTTGGCAAT CTGTGGAAGG TTTGCTCTGG AAAGATTTTA     1500

CATATTTCTA ATGTACATGT ACTAGTCAAG ATACCGATAA CAAAAAAAA                 1549

(2) INFORMATION FOR SEQ ID NO:2:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Lys Phe Leu Ser Ser Leu Val Val Leu Gly Leu Ser Ala Gln Ala
1               5                   10                  15

Leu Ala Ser Pro Tyr Val Asp His Gln Ala Thr Lys Asp Gln Arg Asp
            20                  25                  30

Val Asn Val Phe Lys Gln Val Leu Gln Asp Ile Asn Leu Asp Val Gln
        35                  40                  45

Lys Phe Asp Gln Asp Ile Thr Gln Tyr Gln Gly Gly Asp Pro Thr Val
    50                  55                  60

Leu Leu Ala Asp Ser Asp Ala Ile Ile Lys Thr Thr Glu Glu Gly Ile
65                  70                  75                  80

Gln Arg Ile Gly Pro Gln Pro Pro Leu Ser Val Thr Glu Ala Leu Ala
                85                  90                  95

Leu Val Gly Pro Val Gln Gly Val Asn Lys Leu Ile Met Lys Ala Val
            100                 105                 110

Asp His Leu Ile Glu Lys Lys Gly Pro Leu Val Gly Gly Tyr Gly
        115                 120                 125

Pro Gln Val Lys Asp Ser Leu Glu Arg Gln Ala His Ala Ala Ser Lys
    130                 135                 140

Leu Ser Glu Leu Val Ser Ser Lys Val Pro Ser Pro Leu Ala Pro Ile
145                 150                 155                 160

Ser Lys Gln Leu Ser Asp Gln Val Ala Gln Ala Leu Gln Lys Gly Ile
                165                 170                 175

Gln Ala Phe Ser Ile Ser Ala Arg Gln Ala Thr Lys Val Lys Arg Glu
            180                 185                 190

Ala Thr Lys Val Gln Arg Asp Ile Ser Ala Phe Lys Lys Val Ile Gln
        195                 200                 205

Asn Ile Ser Leu Ala Val Asn Lys Phe Asn Val Asp Ile Glu Arg Tyr
    210                 215                 220

Val Gly Gly Asp Ala Ser His Leu Leu Ala Asp Gly Asn Val Leu Ile
```

-continued

```
225                 230                 235                 240

Lys Ala Thr Leu Asp Gly Val Gln Ser Leu Gln Asn Glu Pro Pro Leu
                245                 250                 255

Ser Ser Met Glu Ala Leu Ala Leu Val Gly Pro Val Gln Asp Leu Ser
            260                 265                 270

Asn Gln Ile Leu Leu Ala Ile Gln Asn Leu Ile Asp Lys Lys Glu Pro
        275                 280                 285

Leu Val Gln Ala Gly Phe Gly Gly Lys Val Glu Asn Asn Leu Arg Gln
    290                 295                 300

Gln Glu Glu Ala Ala Gln Lys Leu Ser Glu Leu Val Ser Thr Lys Val
305                 310                 315                 320

Pro His Glu Leu Ala Asp Ile Ser Arg Gln Leu Ser Asp Gly Ile Ala
                325                 330                 335

Ala Gly Ile Lys Lys Gly Ile Asp Ala Phe Ala Gly Thr Gly Pro Ala
            340                 345                 350

Pro Thr Thr Ser Ser Thr Pro Glu Ala Ser Thr Ala Pro Ala Pro Ser
        355                 360                 365

Thr Pro Pro Gln Thr Pro Glu Asp Thr Leu Val Pro Ala Thr Ser Thr
    370                 375                 380

Pro Ala Pro Gly Pro Ala Pro Thr Ala Pro Asp Ser Ser Met Val Trp
385                 390                 395                 400

Pro Thr Ser Thr Thr Ala Ser Pro Asp Val Gln Pro Thr Ile Thr Ser
                405                 410                 415

Ser Gly Thr Ser Val Pro Ala Ala Pro Thr Gly Gly Asn Ser Ser Pro
            420                 425                 430

Ala Val Pro Ala Phe Thr Gly Ala Ala Ser Ala Asn Gln Val Ser Gly
        435                 440                 445

Ala Val Gly Leu Ala Ala Gly Leu Leu Ala Val Leu Ala Phe
    450                 455                 460
```